United States Patent
Chitre et al.

(10) Patent No.: US 7,181,290 B2
(45) Date of Patent: Feb. 20, 2007

(54) CONVERTIBLE STYLET TO ABET IN THE IMPLANT OF A LEFT HEART LEAD

(75) Inventors: Yougandh Chitre, Valencia, CA (US); David E. Kistler, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 98 days.

(21) Appl. No.: 10/800,372

(22) Filed: Mar. 12, 2004

(65) Prior Publication Data

US 2005/0203603 A1   Sep. 15, 2005

(51) Int. Cl.
*A61N 1/05* (2006.01)
(52) U.S. Cl. .................. 607/122; 607/119; 600/585
(58) Field of Classification Search .......... 607/127, 607/119, 122; 600/585
See application file for complete search history.

(56) References Cited

U.S. PATENT DOCUMENTS

| | | | | |
|---|---|---|---|---|
| 4,498,482 A | * | 2/1985 | Williams | 607/122 |
| 4,727,873 A | * | 3/1988 | Mobin-Uddin | 606/200 |
| 4,798,193 A | * | 1/1989 | Giesy et al. | 600/114 |
| 4,865,037 A | * | 9/1989 | Chin et al. | 607/2 |
| RE33,911 E | * | 5/1992 | Samson et al. | 128/772 |
| 5,129,404 A | * | 7/1992 | Spehr et al. | 607/127 |
| 5,344,439 A | | 9/1994 | Otten | 607/126 |
| 5,489,271 A | * | 2/1996 | Andersen | 604/103.04 |
| 5,527,298 A | | 6/1996 | Vance et al. | 604/280 |
| 5,571,161 A | * | 11/1996 | Starksen | 607/122 |
| 5,662,119 A | * | 9/1997 | Brennen et al. | 600/585 |
| 5,697,965 A | * | 12/1997 | Griffin, III | 607/123 |
| 6,370,434 B1 | | 4/2002 | Zhang et al. | 607/122 |
| 6,389,320 B1 | | 5/2002 | Pianca | 607/122 |
| 6,493,591 B1 | | 12/2002 | Stokes | 607/127 |
| 6,944,506 B1 | * | 9/2005 | Morgan et al. | 607/122 |
| 2002/0077685 A1 | | 6/2002 | Sundquist et al. | 607/116 |
| 2003/0191515 A1 | * | 10/2003 | Haldeman et al. | 607/119 |
| 2005/0070986 A1 | | 3/2005 | Tockman et al. | 607/122 |

FOREIGN PATENT DOCUMENTS

| | | |
|---|---|---|
| WO | WO 91/19528 | 12/1991 |
| WO | WO 94/13350 | 6/1994 |
| WO | WO 2004/067078 A2 | 8/2004 |
| WO | WO 2004/067078 A3 | 8/2004 |

* cited by examiner

*Primary Examiner*—Robert Pezzuto
*Assistant Examiner*—Shevon Johnson

(57) ABSTRACT

To implant a lead system for an implantable cardiac stimulation device, a guide wire is slidably introduced into a longitudinally extending internal passage of an elongated stylet. In turn, the combined stylet and guide wire are slidably introduced into the longitudinally extending lumen of an elongated tubular lead body of flexible resilient insulative material having a thrusting region near its distal end. With the distal end of the stylet in engagement with the thrusting region of the lead, the stylet together with the lead and guide wire are advanced until the lead should encounter a tortuous turn in the vasculature of the body. At this point, the guide wire is advanced through the stylet and into the vasculature until the distal end of the guide wire arrives at a chosen location. The stylet then re-continues its advance together with the lead until the lead reaches the desired implant location.

7 Claims, 4 Drawing Sheets

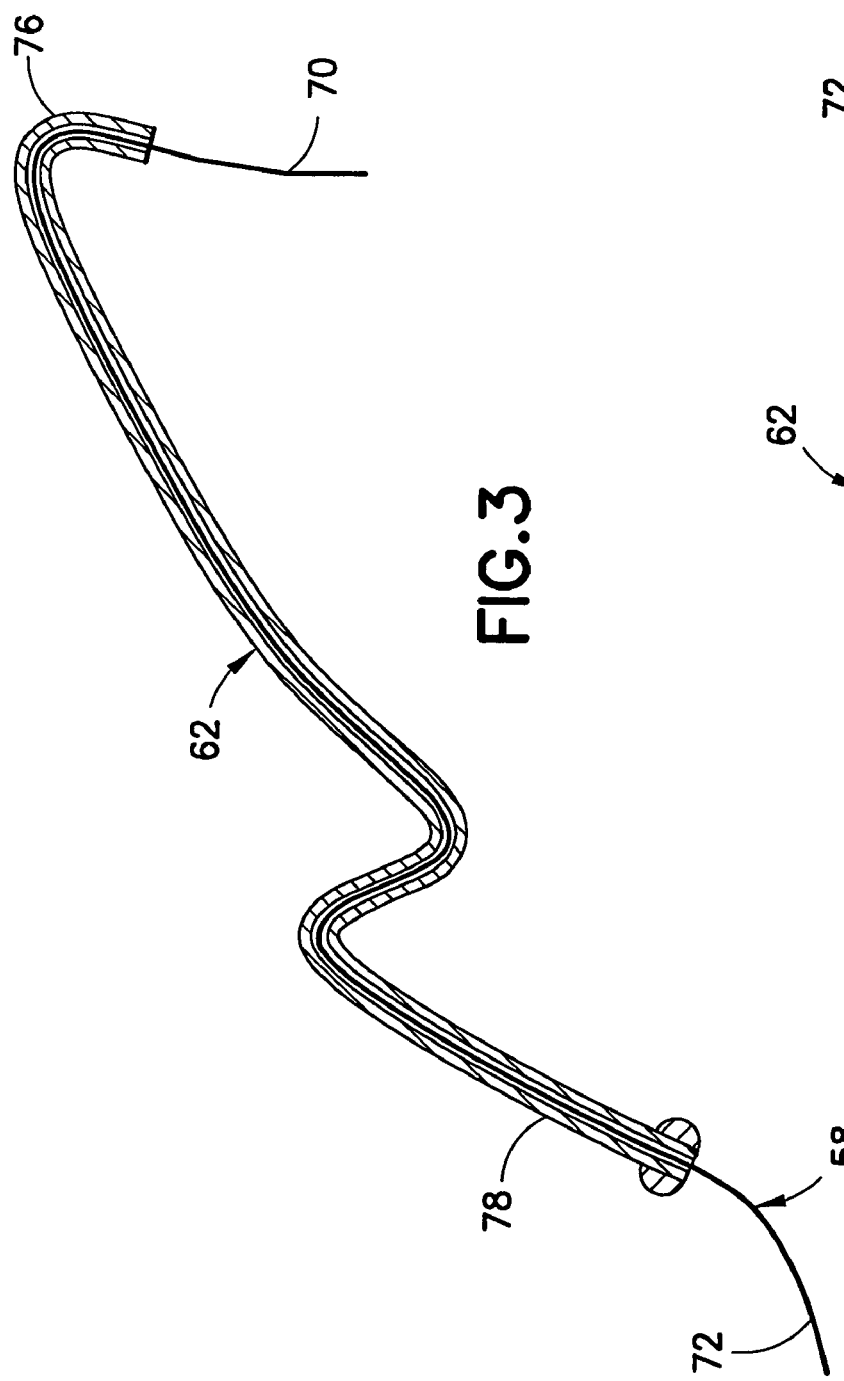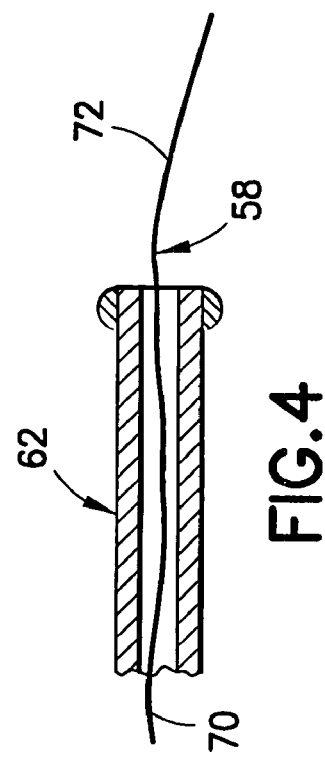

CONVERTIBLE STYLET TO ABET IN THE IMPLANT OF A LEFT HEART LEAD

FIELD OF THE INVENTION

The present invention generally relates to the implantation of stimulation leads for use with implantable cardiac stimulation devices. The present invention more particularly relates to a technique which enables, selectively, either stylet placement or guide wire placement.

BACKGROUND

Implantable cardiac stimulation devices are well known in the art. Such devices may include, for example, pacemakers or defibrillators. These devices are generally implanted in an upper portion of the chest beneath the skin of a patient within what is known as a subcutaneous pocket.

Traditionally, therapy delivery has been limited to the right side of the heart. To that end, one or more stimulation leads are implanted within the heart. The leads may include one or more electrodes positioned within the right ventricle or right atrium, or both, of the heart for making electrical contact with their respective heart chambers. Conductors within the leads couple the electrodes to the device to enable the device to deliver the desired cardiac stimulation therapy.

Recently, cardiac stimulation leads and methods have been proposed and even practiced for delivering cardiac stimulation therapy from or to the left side of the heart. These lead structures and methods involve lead implantation within the coronary sinus and/or the great vein of the heart and/or coronary sinus veins, for example, since the coronary sinus is closely adjacent the left atrium and extends into the great vein which is adjacent the left ventricle of the heart. Electrodes thus placed in the coronary sinus and great vein may be used for various forms of cardiac stimulation therapy such as left atrial pacing, left ventricular pacing, and even cardioversion and defibrillation, for example.

Cardiac stimulation lead placement within the left side of the heart can require lead placement in difficult-to-reach veins and arteries. Two methods generally practiced for lead placement are stylet placement and guide wire placement. Stylet placement is a common practice for lead placement in the right side of the heart. Guide wire placement is less commonly employed.

Currently, there is debate in the art as to which lead placement method is best for lead placement in the left side of the heart. Each has its advantages and disadvantages. Stylet placement has the advantage of simplicity and involves minimal components, sometimes an important factor during a surgical procedure. In some patients with small veins or unusual cardiac vein anatomy, the guide wire placement method may have an advantage in facilitating lead placement. It is likely that both methods will find future use.

Cardiac stimulation leads are designed for only a specific lead placement methodology. More specifically, such leads are configured for either stylet placement or guide wire placement, but usually not both. Unfortunately, this may result in a physician finding, during an implant procedure, that a lead already attempted to be implanted must be discarded in favor of a lead designed for a different implanting method. This not only represents additional cost, but it also can complicate the surgical procedure.

The present invention provides an elegant solution to the aforementioned problem. In one embodiment, the concomitant use of a stylet and guide wire may be employed for implanting a stimulation lead. Not only is a lead so adaptable, the adaptation may be easily made, requires minimal components, and may be accomplished with tools already made available to the surgeon.

In order to fully appreciate the advance provided by the present invention, it is desirable to review the state of the prior art prior to its conception. Known constructions of leads and their manner of implantation can be found in U.S. Pat. No. 5,489,271 to Andersen, U.S. Pat. No. 5,527,298 to Vance et al. and to U.S. Pat. No. 6,389,320 to Pianca.

Andersen discloses a stylet and hub assembled for stiffening a catheter in rapid exchange mode. The catheter guide wire lumen has a side port associated with a bi-stable guide element that lies across the lumen. A disengageable feature assembly limits insertion of the stylet into the lumen in rapid exchange mode. To convert from rapid exchange mode, disengagement of the disengageable feature enables the stylet to displace the guide element, clearing the guide wire lumen and enabling guide wire or other device to extend throughout the lumen.

Vance et al. disclose a guide wire for placement within a blood vessel for penetrating an occlusion in the vessel. The guide wire comprises a length of flexible wire having a concentric lumen running its entire length. At its proximal end, the wire has an opening to the lumen. At its distal end, the wire has an arcuate tip with a diameter greater than the diameter of the wire immediately proximal thereto. In addition, the guide wire may include a flexible stylet substantially the same length as the guide wire that is removably inserted into the lumen of the guide wire. Such stylet placement provides a greater stiffness and structural integrity to the guide wire. Finally a method of penetrating an occlusion in a blood vessel is disclosed which comprises inserting the guide wire into an occluded blood vessel.

Pianca discloses an implantable stimulation lead readily adaptable for stylet placement or guide wire lead placement. The implantable lead includes at its distal end an implanting guide structure which includes a rigid member having a through bore. A plug is dimensioned to be received within the through bore and a retaining mechanism releasably retains the plug within the through bore. When the plug is retained within the through bore, the lead is adapted for stylet placement and when the plug is released from the through bore, the lead is adapted for guide wire lead placement. In a preferred embodiment, the distal electrode of the lead provides the rigid member of the implanting guide structure. After the lead is positioned by guide wire lead placement, the proximal end of the lead may be sealed with a plug or the plug of the implanting guide structure or new plug may be replaced or placed in the lead to prevent blood flow through the lead.

It was in light of the foregoing known apparatus and techniques that the present invention was conceived and has now been reduced to practice.

SUMMARY

According to one illustrative embodiment, to implant a lead system for an implantable cardiac stimulation device, a guide wire is slidably introduced into a longitudinally extending internal passage of an elongated stylet. In turn, the combined stylet and guide wire are slidably introduced into the longitudinally extending lumen of an elongated tubular lead body of flexible resilient insulative material having a thrusting region near its distal end. With the distal end of the stylet in engagement with the thrusting region of the lead, the stylet together with the lead and guide wire are advanced until the lead should encounter a tortuous turn in the vasculature of the body. At this point, the guide wire is advanced through the stylet and into the vasculature until the distal end of the guide wire arrives at a chosen location. With the guide wire bridging the tortuous turn in the vasculature of the body, the stylet then re-continues its advance together with the lead until the lead reaches the desired implant location. It may then be desirable to impart force to the stylet acting against the thrusting region of the lead to wedge the distal end of the lead into place at the desired implant location. Thereafter, the guide wire and the stylet are withdrawn from the vasculature and the lead remains in its chosen location.

To perform this technique, the guide wire includes a proximal tube and an integral distal coil coaxial with the proximal tube and extending distally from the proximal tube. This construction enables the guide wire to advance through a tortuous route often required by the vasculature. Also, preferably, the stylet includes a ball member at its distal end to reduce the possibility of perforating the vasculature as it is advanced. The ball member is preferably stainless steel and welded to the distal end of the stylet preferably composed of stainless steel.

With the onset of multi chamber pacing for Congestive Heart Failure (CHF), there has been much discussion and debate in the medical community as to what is the most desirable lead possible for left ventricular (LV) stimulation. The overwhelming opinion of physicians seems to be that the "best" LV lead is the one that is easiest to place and involves the fewest procedures and parts. As a result of recent advancements in techniques and instrumentation, many physicians have become convinced that a lead that is placed with a guide wire, instead of a stylet, is superior. However, more often than not, an implanter may choose to use a combination of a stylet and guide wire in the placement of an LV lead. This requires a constant change out of either a stylet and/or guide wire.

In short, what is described herein is a "convertible stylet", designed to streamline the implant procedure of an LV lead.

This design teaches the concept of a stylet that accommodates a lumen for the passage of a guide wire. Suitable materials will be employed for the stylet and guide wire to ensure that the pushability of the stylet and flexibility of the guide wire are not compromised. A ball-tipped stylet end ensures that the stylet does not perforate a vein.

The combination of the lead, stylet, and guide wire can be introduced into the vasculature. Selective use of either the stylet and/or guide wire aids in the implant of the lead at an optimal site. By virtue of design, the need for change-out of the stylet and/or guide wire is eliminated.

The implant procedure could entail the following:
the LV lead accommodating the stylet and guide wire is introduced into the vasculature;
the stylet can be employed to push the lead until a tortuous turn is encountered;
the guide wire strung through the stylet a priori can be advanced to a desired implant site
the LV can be then be tracked over the guide wire to the desired implant location; and
the stylet can then be employed to wedge the distal end of the lead in place or double up as a "finishing stylet" to ensure that the distal end of the lead is not displaced from its optimal location when the guide wire is withdrawn.

Other and further features, advantages, and benefits will become apparent in the following description taken in conjunction with the following drawings. It is to be understood that the foregoing general description and the following detailed description are exemplary and explanatory but are not to be restrictive. The accompanying drawings which are incorporated in and constitute a part of this invention, illustrate one illustrative embodiment, and together with the description, serve to explain the illustrative embodiment in general terms. Like numerals refer to like parts throughout the disclosure.

BRIEF DESCRIPTION OF THE DRAWINGS

FIG. 3 is a diagrammatic perspective view illustrating a combination of guide wire and stylet;

FIG. 4 is a detail side elevation view, in section, illustrating a combination of guide wire and stylet;

DETAILED DESCRIPTION OF THE PREFERRED EMBODIMENTS

Figure 1:
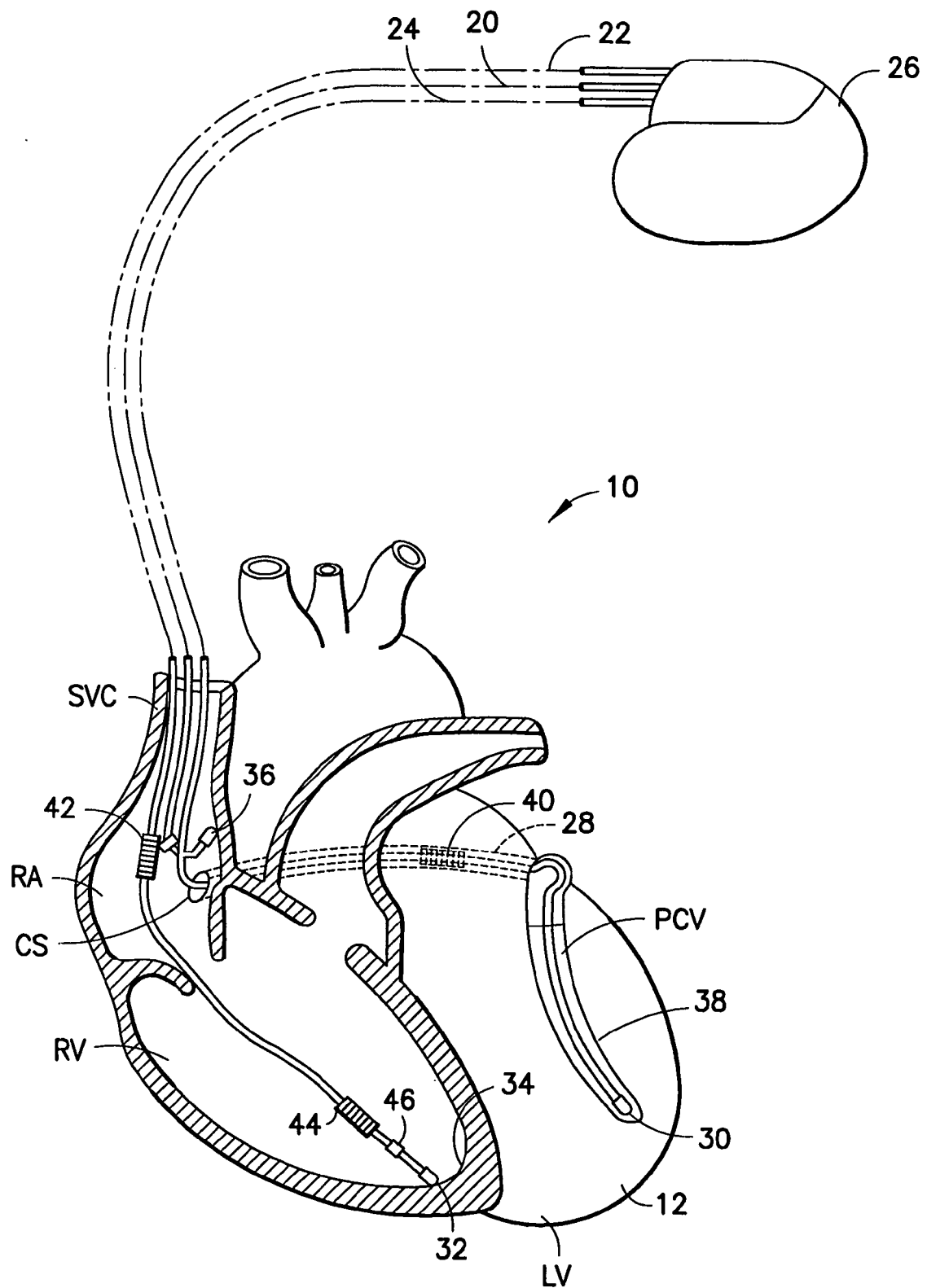
FIG. 1 is a diagrammatic perspective view illustrating an implanted lead system for providing electrical stimulation of a heart.

Refer now to the drawings and, initially, to FIG. 1 in which is shown a diagrammatic perspective view of an implanted system 10 for providing electrical stimulation of a heart 12 and depicting one illustrative embodiment. Although several embodiments will be described and shown in the drawings, it should be understood that the present invention can be embodied in many alternate forms or embodiments. In addition, any suitable size, shape or type of elements or materials could be used.

In FIG. 1, implantable leads 20, 22, 24 are illustrated generally embodying apparatus for stimulation of the body, the heart 12 in this instance, by means of a pacemaker 26 or other suitable pulse generating or stimulating device. This is a cross section view of a human heart showing the right atrium RA and the right ventricle RV along with the coronary sinus CS and a vein 28 of the left side of the heart. This vein of the left side could be any of the veins found on the left side of the heart such as the great cardiac vein, posterior vein, or the lateral vein of the left ventricle LV. The leads are shown in a typical placement, lead 20 being an RA lead, lead 22 being an RV lead, and lead 24 being an LV lead inserted via the superior vena cava SVC into the coronary sinus ostium CSO located in the right atrium RA. The lead 24 is then advanced through the coronary sinus ostium, passing through the coronary sinus, and placed into a tributary of the coronary venous system, preferably the left posterior cardiac vein PCV with an associated tip electrode 30 being placed deep in the distal portion of the left side of the heart. The phrase "coronary venous system" refers to the coronary sinus vein, great cardiac vein, left marginal vein, left posterior vein, middle cardiac vein, and/or small cardiac veins or any other cardiac vein accessible by the coronary sinus. From this location, the lead 24 can be used to stimulate the left ventricle LV. Clearly, the lead 24 must follow a tortuous path in order for the tip electrode 30 to reach its intended destination. The lead 22 extends to a tip electrode 32 placed in the apex 34 of the right ventricle RV and illustrates the typical position of a lead in the right ventricle. The lead 20 extends to a tip electrode 36 shown in the appendage of the right atrium RA and illustrates the typical position of the lead in the appendage of the right atrium. In this scenario, component 38 is typical of a sensing electrode of the LV lead 24, component 40 is typical of a shock electrode of the LV lead 24, component 42 is typical of a proximal shock coil of the RV lead 22, component 44 is typical of a distal shock coil of the RV lead 22 and component 46 is typical of a ring electrode of the RV lead 22.

It was earlier explained that as a result of recent advancements in techniques and instrumentation, many physicians have become convinced that a lead that is placed with a guide wire, instead of a stylet, is superior. However, more often than not, an implanter may choose to use a combination of a stylet and guide wire in the placement of an LV lead. The thrust of the present invention, therefore, is to mitigate the switching out of the stylet and/or guide wire, employed in the implant of a LV lead.

Leads that are used with guide wires to gain access to the coronary venous system must have an open lumen at the distal tip of the lead to allow the guide wire to pass through. In this regard, turn now to FIG. 2. Here, a stimulating lead 48 is illustrated as including a coil conductor 50 coupled to a distal electrode 52, the conductor being surrounded by an insulating sheath 54 of suitable flexible, resilient, insulative material. The distal electrode 52 has an aperture 56 for reception therethrough of a guide wire 58 for use in implanting the lead. However, when an implanting physician finds that the guide wire method is not successful, it is possible that the present invention can be successfully used.

To this end, an enlarged distal tip end 60 of a stylet 62 passes through a lumen 64 of the lead but stops at the distal electrode 52. More specifically, the distal electrode 52 is formed with a proximally facing bearing surface 66, or thrusting region, for engageably receiving the distal tip end 60 of the stylet 62. To assure this result, the distal tip end 60 has a width greater than that of the aperture 56 of the distal electrode 52 with the result that the stylet can selectively be used for implanting the lead system in place of the guide wire. This prevents the enlarged distal tip of the stylet from proceeding through the distal tip of the lead 48 and causing undesirable consequences such as perforation of the vein into the pericardial sac, which in turn can cause tamponade. Indeed, the distal tip end of the stylet 62 is similarly enlarged, including a ball member 68 at its distal end to reduce the possibility of perforating the vasculature. Preferably, the ball member is composed of stainless steel and welded to the distal end of the stylet which is also preferably composed of stainless steel.

Figure 2:
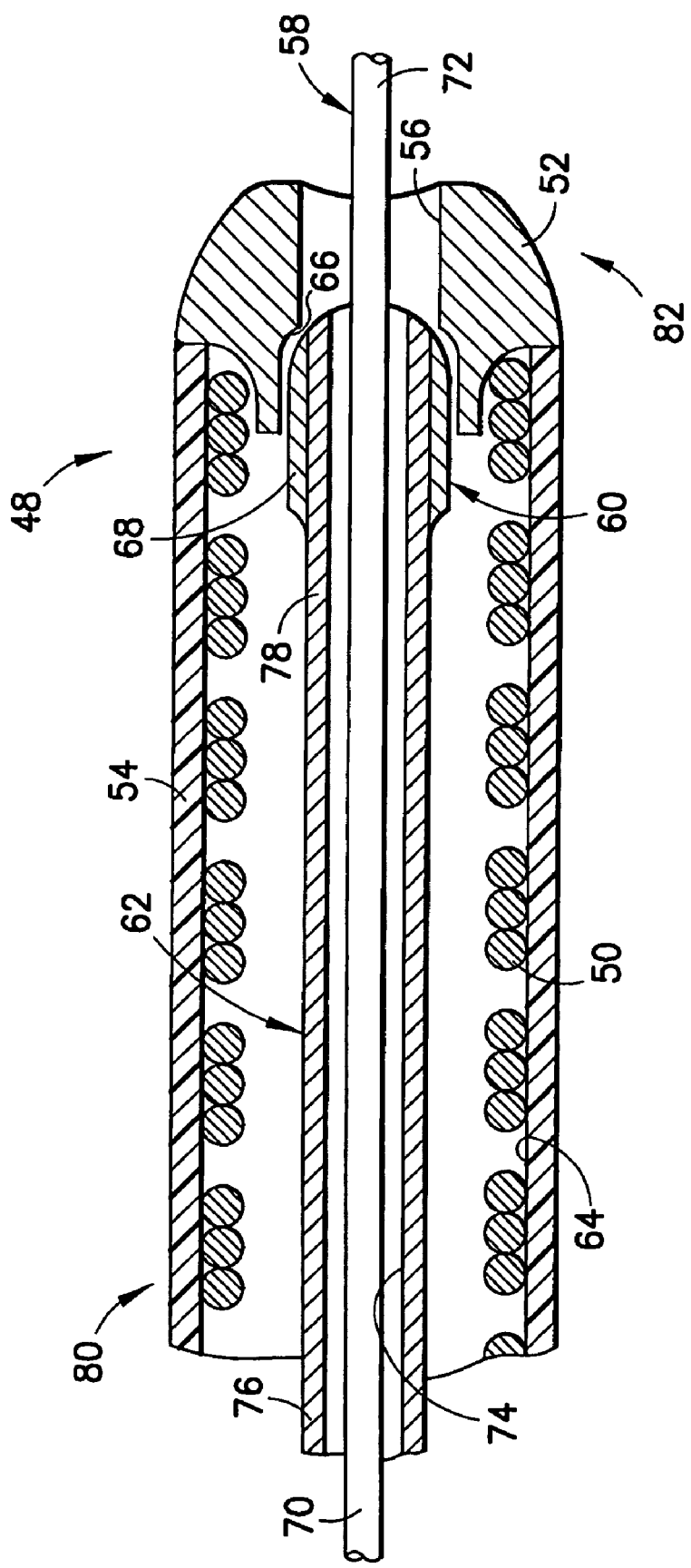
FIG. 2 is a detail longitudinal cross sectional view of the distal end of a lead system employing a combination of guide wire and stylet for the implanting operation.

According to the preferred technique of the invention, especially viewing FIGS. 2, 3, and 4, the guide wire 58 extending between proximal and distal ends 70, 72, respectively, is introduced into a longitudinally extending internal passage 74 of the stylet 62, itself extending between proximal and distal ends 76, 78, respectively. Thereupon, the combination of the stylet 62 and guide wire 58 are introduced into the longitudinally extending lumen 64 of the lead 48 which also extends between proximal and distal ends 80, 82, respectively. With the distal tip end 60 of the stylet 62 in engagement with the bearing surface 66 or thrusting region of the lead 48, the stylet together with the lead and guide wire are advanced until such time that the lead encounters a tortuous turn in the vasculature of the body.

If or when that occurs, the guide wire 58 is advanced through the stylet 62 and into the vasculature until the distal end 72 of the guide wire 58 arrives at a chosen location. At this point, with the guide wire 58 bridging the tortuous turn in the vasculature of the body, once again, the stylet proceeds and continues to advance together with the lead 48 since the distal tip end 60 is engaged with the bearing surface 66. Such advance continues until the lead 48 reaches the desired implant location.

When the desired implant location is reached, additional force is desirably imparted to the stylet 62 acting against the thrusting region 66 of the lead 48 to wedge the distal end 82 of the lead 48 into place at the desired implant location.

Thereafter, the guide wire 58 is withdrawn from the vasculature and likewise the stylet.

Figure 5:
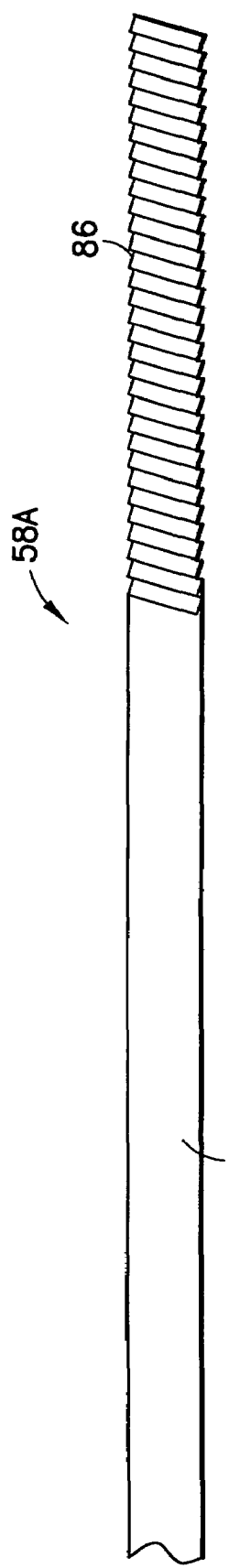
FIG. 5 is a detail side elevation view illustrating a portion of one embodiment of guide wire.

For this procedure, the guide wire 58 may assume different constructions. In one instance, viewing FIG. 5, a guide wire 58A includes a proximal shaft 84 and an integral distal coil 86 coaxial with the proximal shaft and extending distally from the proximal shaft. The shaft construction provides superior pushability of the guide wire.

Figure 6:
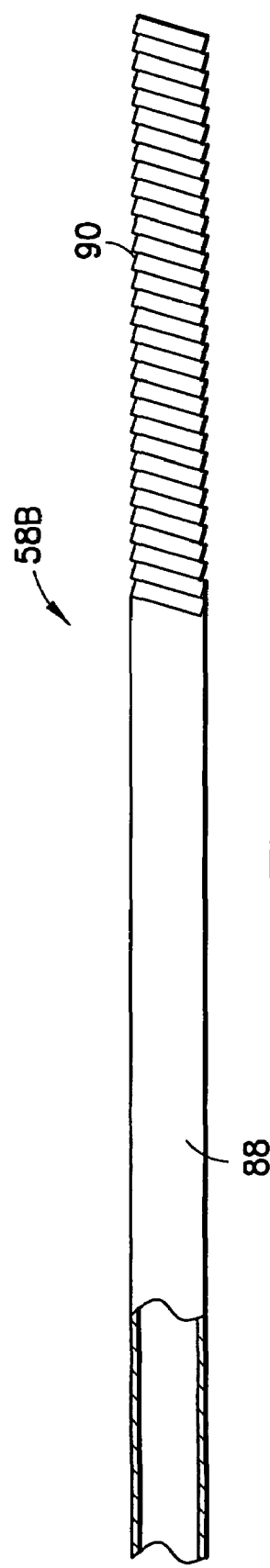
FIG. 6 is a detail side elevation view illustrating a portion of another embodiment of guide wire.

In another instance, viewing FIG. 6, a guide wire 58B includes a proximal tube 88 and an integral distal coil 90 coaxial with the proximal tube and extending distally from the proximal tube. The tubular construction provides a lumen for the introduction of contrast dye whenever desired. In each instance, the distal coil serves to more easily navigate the tortuous vasculature.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. A lead implant system for implanting a lead for an implantable cardiac stimulation device, the lead implantation system comprising:
    an elongated stylet having an internal passage extending longitudinally through the stylet; and
    a guide wire that is slidably receivable through the longitudinally extending passage of the stylet, the combined stylet and guide wire being configured for slidable introduction into an elongated tubular lead body for cooperatively implanting a distal end of the lead at a desired location, and wherein the guide wire is configured for extension beyond a distal end of the stylet.

2. The lead implant system set forth in claim 1:
    wherein the stylet is configured to be firmly engaged with a thrusting region of the lead to wedge the distal end of the lead into place at the desired implant location.

3. The lead implant system set forth in claim 1:
    wherein the guide wire comprises:
    a proximal shaft; and
    an integral distal coil coaxial with the proximal shaft and extending distally from the proximal shaft.

4. The lead implant system set forth in claim 1:
    wherein the guide wire comprises:
    a proximal tube; and
    an integral distal coil coaxial with the proximal tube and extending distally from the proximal tube.

5. The lead implant system set forth in claim 1:
    wherein the stylet includes a ball member at its distal end to reduce the possibility of perforating the vasculature.

6. The lead implant system set forth in claim 1:
    wherein the stylet is composed of stainless steel and the ball member is stainless steel welded to the distal end of the stylet.

7. The lead implant system of claim 1 for use with a lead that defines an opening in a distal portion of the lead, and wherein the guide wire is configured for extension through the opening in the distal portion of the lead.

* * * * *